United States Patent [19]

Hirai et al.

[11] Patent Number: 4,523,031

[45] Date of Patent: Jun. 11, 1985

[54] PROCESS FOR PRODUCING A PARA-SUBSTITUTED PHENOL DERIVATIVE

[75] Inventors: Hidefumi Hirai; Makoto Komiyama, both of Tokyo, Japan

[73] Assignee: Asahi Kasei Kogyo Kabushiki Kaisha, Osaka, Japan

[21] Appl. No.: 530,158

[22] Filed: Sep. 7, 1983

Related U.S. Application Data

[63] Continuation-in-part of Ser. No. 385,405, May 17, 1982, abandoned.

[30] Foreign Application Priority Data

Aug. 11, 1981 [JP] Japan .............................. 56-125558
Aug. 13, 1981 [JP] Japan .............................. 56-127077

[51] Int. Cl.³ ............................................. C07C 65/04
[52] U.S. Cl. .................................. 562/475; 562/508; 568/377; 568/657; 568/813
[58] Field of Search ................ 562/475, 508; 568/377, 568/657, 813

[56] References Cited

PUBLICATIONS

Ohara, M. et al., Pharmazie, vol. 33, No. 7, (1978), p. 467.
Chemical Review, 60, 169 (1960).
J. Amer. Chem. Soc., 81, 6446 (1959).
Pharmazie, 33, H, 7 (1978).

*Primary Examiner*—Paul J. Killos
*Attorney, Agent, or Firm*—Sprung, Horn, Kramer & Woods

[57] ABSTRACT

By reacting, using as a catalyst a modified or unmodified cyclodextrin, a phenol compound with an organic halide selected from the group consisting of a carbon tetrahalide and a substituted or unsubstituted allyl halide in the presence of an alkali metal hydroxide, a substituent group derived from said organic halide can be introduced to the para-position of the phenol compound with high selectivity, whereby various useful para-substituted phenol derivatives can be advantageously obtained.

10 Claims, No Drawings

PROCESS FOR PRODUCING A PARA-SUBSTITUTED PHENOL DERIVATIVE

This application is a continuation-in-part of our U.S. patent application Ser. No. 385,405 filed on May 17, 1982 now abandoned.

This invention relates to a process for producing a para-substituted phenol derivative with high selectivity. More particularly, the present invention is concerned with a process for producing a para-substituted phenol derivative which comprises reacting a phenol compound with an organic halide selected from the group consisting of a carbon tetrahalide and a substituted or unsubstituted allyl halide in the presence of an alkali metal hydroxide, using a cyclodextrin as a catalyst.

It is known that para-hydroxybenzoic acid derivatives are prepared by reacting a phenol with a carbon tetrahalide under alkaline conditions. 2,5-Cyclohexadienone derivatives having a substituted or unsubstituted allyl group at the 4-position have conventionally been prepared in a process comprising two steps which will be explained later. The products thus obtained are extremely valuable compounds as pharmaceuticals, agricultural chemicals, or raw materials for polymers, various physiologically active substances such as agricultural chemicals and pharmaceuticals, and dyes.

However, known reaction processes have serious disadvantages of extremely low selectivity and therefore poor yield. Accordingly, the known process cannot be advantageously used in practice.

For example, as to the production of para-hydroxybenzoic acid which, nowadays, is of increasing importance as a raw material for heat resistant polymers, agricultural chemicals and pharmaceuticals, known is the Kolbe-Schmitt reaction in which para-hydroxybenzoic acid is synthesized by treating phenol with potassium hydroxide and potassium carbonate, followed by heating together with carbon dioxide under elevated pressure. The reaction, however, has disadvantages that a costly pressure resistant apparatus is required because of high pressure applied during the reaction, and that much energy is required for the achievement of an absolute anhydrous condition which is indispensable to the reaction. Also known is another process in which phenol is reacted with a carbon tetrachloride in the presence of an alkali metal hydroxide to prepare para-hydroxybenzoic acid. In the process, however, the selectivity for the formation of para-hydroxybenzoic acid is 57%, and the reaction gives a large amount of salicylic acid as a by-product. Therefore, the process also requires not only large amounts of raw materials but also an operation for separation.

2,5-Cyclohexadienone derivatives having an allyl group at the 4-position are also highly reactive due to the conjugation of two C-C double bonds and a carbonyl group. In addition, they have an allyl group at such a position that an intramolecular ring-forming reaction is readily caused to occur. Accordingly, the derivatives are valuable compounds as starting materials for preparing physiologically active substances and other useful substances. 2,5-Cyclohexadienone derivatives having an allyl group at the 4-position have conventionally been prepared in a process comprising two steps, namely, the first step in which a 1:1 mixture of sodium methoxide and a para-substituted phenol is reacted with an allyl halide in an aromatic solvent to produce a 2,4-cyclohexadienone derivative which is allyl-substituted at the 6-position, and the second step in which the product in the first step is then reacted in a methanol-hydrochloric acid mixture to allow the allyl group to transfer to the 4-position. The process has disadvantages that the 2,4-cyclohexadienone derivative which is a reaction product of the first step is difficult to separate and purify, and that the reactions involved in the process require large amounts of organic solvents.

As described above, any of the conventional processes for introducing a substituent derived from an organic halide selected from a carbon tetrahalide and a substituted or unsubstituted allyl halide to the para-position of phenols are unsatisfactory from a practical point of view because of extremely low selectivity or because of necessity of two reaction steps accompanied by other difficulties during the reaction.

The present inventors have made extensive and intensive studies to develop a process in which a substituent derived from an organic halide selected from a carbon tetrahalide and a substituted or unsubstituted allyl halide (hereinafter often referred to simply as "organic halide") is intoduced to the 4-position of phenols with high selectivity to give intermediates for the produciton of various useful substances as mentioned above. As a result, it has been found that, when a phenol compound is reacted with an organic halide in the presence of cyclodextrin under an alkaline condition, a substituent group derived from said organic halide is introduced to the 4-position of the phenol compound with high selectivity, and therefore the intended para-substituted phenol derivative can be obtained in high yield. Based on such a novel finding the present invention has been made.

Accordingly, it is an object of the present invention to provide a process for producing a para-substituted phenol derivative with high selectivity.

The foregoing and other objects, features and advantages of the present invention will be apparent to those skilled in the art from the following detailed description and appended claims.

According to the present invention, there is provided a process for producing a para-substituted phenol derivative which comprises reacting a phenol compound represented by the formula(I)

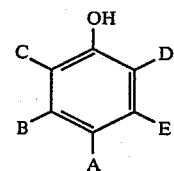

wherein A, B, C, D and E each independently stand for hydrogen, a hydroxyl group, a substituted or unsubstituted alkyl group, a substituted or unsubstituted allyl group, a substituted or unsubstituted alkoxyl group or a substituted or unsubstituted aryl group, provided that A does not stand for a hydroxyl group and that when two or more of A, B, C, D, and E each independently stand for a substituted or unsubstituted alkyl group or a substituted or unsubstituted alkoxyl group, they have their respective free terminal ends or at least one of them is bonded to another group selected from said alkyl and alkoxyl groups to form a ring, with an organic halide selected from the group consisting of a carbon tetrahalide and a substituted or unsubstituted allyl halide in the presence of an alkali metal hydroxide, using as a catalyst a modified or unmodified cyclodextrin, thereby to introduce a substituent group derived from said organic halide to the para-poisiton of the phenol compound.

By the term "phenol compound" as used herein is meant phenol (hydroxybenzene) or its derivative which is defined by the above-mentioned formula(I). The substituted or unsubstituted alkyl group, the substituted or unsubstituted allyl group, the substituted or unsubstituted alkoxyl group and the substituted or unsubstituted aryl group each may preferably have carbon atoms of not more than 6 with respect to the substituents B, C, D and E, and each may preferably have carbon atoms of not more than 12 with respect to the substituent A.

As the substituent to be introduced to the alkyl group, allyl group, alkoxyl group and aryl group, there can be mentioned an alkyl group, a halogen atom and others without specific restriction. However, too large a group is undesired.

The organic halide which is one of the reactants to be used in the process of the present invention is selected from the group consisting of a carbon tetrahalide and a substituted or unsubstituted allyl halide. The substituted or unsubstituted allyl halide may preferably have carbon atoms of not more than 12. As such an allyl halide, the chloride and bromide are especially preferred. The organic halide may be used in an amount of 1 to 20 mols, preferably 1.5 to 10 mols per mol of the phenol compound used.

The alkali metal hydroxide to be used in the process of the present invention may preferably be sodium hydroxide or potassium hydroxide. The alkali metal hydroxide may be used in a stoichiometrical amount relative to the phenol compound. Usually, however, 1 to 15 times, preferably 1.5 to 10 times the stoichiometrical amount of the alkali metal hydroxide may be used taking into consideration of the rate of reaction and the like.

The reaction according to the process of the present invention is usually carried out in a reaction medium. As the reaction medium, there is employed an aqueous solvent, preferably water, because of the requirement that the reaction medium be capable of dissolving the alkali metal hydroxide therein. There may also be used, as the reaction medium, a mixture of water with a small amount of an organic solvent which is soluble in water and can be present stably under the reaction conditions. Examples of such an organic solvent include methanol, ethanol, acetone, dimethoxyethane and the like. The concentration of the alkali metal hydroxide in the reaciton solvent may be in the range of 0.1 to 30% by weight, preferably 0.5 to 25% by weight.

As mentioned above, a modified or unmodified cyclodextrin is used as a catalyst in the process of the present invention. Any of modified or unmodified $\alpha$-, $\beta$- and $\gamma$-cyclodextrins may be used. Usually, satisfactory results can be obtained by the use of unmodified $\alpha$-, $\beta$- or $\gamma$-cyclodextrin. However, a more improved yield and selectivity in the reaction are achieved by the use of a modified $\alpha$-, $\beta$- or $\gamma$-cyclodextrin of which the primary hydroxyl groups, for example, are all or partly substituted with a group which is stable under alkaline conditions, such as a N-methylformamido group. Particularly, when the organic halide is a substituted or unsubstituted allyl halide, the use of a modified cyclodextrin exhibits an excellent yield and selectivity in the reaction as compared with the use of an unmodified cyclodextrin. The abovementioned modified cyclodextrin may be prepared according to the method described in J. Amer. Chem. Soc., 102, 762 (1980). The modified or unmodified cyclodextrin (hereinafter often referred to simply as "cyclodextrin") may be employed in an amount of 0.001 to 20 in terms of molar ratio with respect to the organic halide used. A more preferable molar ratio of a cyclodextrin to an organic halide varies depending on the kind of an organic halide to be used. Specifically, where the organic halide is a carbon tetrahalide, the molar ratio of a cyclodextrin to a carbon tetrahalide is preferably 0.001 to 5, more preferably 0.01 to 1. Where the organic halide is a substituted or unsubstituted allyl halide, the molar ratio of a cyclodextrin to an allyl halide is preferably 0.01 to 20, more preferably 0.1 to 5.

In practicing the process of the present invention, all the amount of the organic halide to be used may be added to a solution containing a phenol compound, an alkali metal hydroxide and a cyclodextrin at the time of initiation of the reaction. Alternatively, an organic halide may be added to a system comprising a phenol compound, an alkali metal hydroxide and a cyclodextrin so that the molar ratio of a cyclodextrin to an organic halide is maintained at a value falling within the range as mentioned above. The latter mode of process can be practiced by intermittently or gradually adding an organic halide to the above-mentioned system. In this mode of process, the molar ratio of a cyclodextrin to an organic halide can be easily maintained at a value within the above-mentioned range even by the use of a small amount of cyclodextrin, leading to economical advantages. In this case, the control of the molar ratio of the cyclodextrin to the organic halide in the reaction system may be made by the following method. At a predetermined time interval during the course of the reaction, part of the reaction mixture is taken, subjected to the determination of the organic halide contained therein by gas chromatography, and the rate of the addition of the organic halide to the reaction system is adjusted so that the molar ratio of the cyclodextrin to the organic halide is maintained at a value falling within the range as mentioned above.

When the reaction of a phenol compound with an organic halide is effected while maintaining the molar ratio of the cyclodextin to the organic halide in the reaction system at a value within the range as mentioned above, the amount of the cyclodextrin relative to the amount of the phenol compound used is not critical as far as the molar ratio of the cyclodextrin to the organic halide in the reaction system and the molar ratio of the organic halide to the phenol compound are within the ranges as mentioned above. But, in general, the cyclodextrin may be used in an amount of 0.0001 to 10 in terms of molar ratio with respect to the phenol compound used. A preferable molar ratio of a cyclodextrin to a phenol compound varies depending on the kind of an organic halide to be used. Specifically, where the organic halide is a carbon tetrahalide, the molar ratio of a cyclodextrin to a phenol compound is preferably 0.0001 to 1, more preferably 0.01 to 0.5. Where the organic halide is a substituted or unsubstituted allyl halide, the molar ratio of a cyclodextrin to an allyl halide is preferably 0.01 to 10, more preferably 0.1 to 5.

The reaction temperature is not critical, and may be suitably determined according to a phenol compound to be used, but generally is 0° to 120° C., preferably 20° to 100° C.

The reaction time is also not critical, and may be suitably determined according to the kinds of a phenol compound and an organic halide to be used, the amounts of reactants, reaction temperature, manner of addition of reactants and the like but generally is 10 minutes to 40 hours.

The reaction pressure is also not restricted, and the reaction is usually carried out at atmospheric pressure from a viewpoint of ease in operation.

By the reaction of the phenol compound with the organic halide according to the process of the present invention, there is produced a para-substituted phenol derivative of the kind varied depending on the kinds of the phenol compound and the organic halide, as described later.

From phenol compounds of the formula(I) in which A is a hydrogen atom, para-hydroxybenzoic acids, or para-allyl phenols are obtained.

From phenol compounds of the formula(I) in which A is other substituent than hydrogen, namely, a substituted or unsubstituted alkyl group, a substituted or unsubstituted allyl group, substituted or unsubstituted alkoxyl group or substituted or unsubstituted aryl group, there is obtained 4-allyl-2,5-cyclohexadienone derivatives. Illustratively stated, when A in the formula(I) is hydrogen, there is obtained a para-substituted phenol deviative represented by the formula (II)

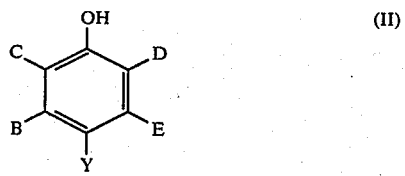

(II)

wherein B, C, D and E are as defined above and Y stands for a substituted or unsubstituted allyl group or a carboxyl group, whereas when A in the formula(I) is a substituted or unsubstituted alkyl group, a substituted or unsubstituted allyl group, a substituted or unsubstituted alkoxyl group or a substituted or unsubstituted aryl group, there is obtained a para-substituted phenol derivative represented by the formula(III)

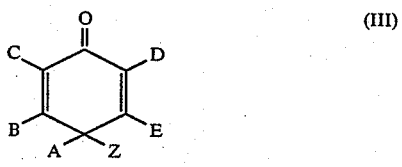

(III)

wherein A, B, C, D and E are as defined above, provided that A does not stand for hydrogen, and Z stands for a substituted or unsubstituted allyl group. As is apparent from the foregoing, according to the process of the present invention, a variety of useful phenol derivatives having a substituent introduced to the para-position thereof are produced form phenols with high selectivity. Therefore, not only can be reduced the required amounts of phenols as raw materials but also the purification process can be extremely simplified, thus enabling the production process of the desired products to be economic.

The present invention will be illustrated in more detail with reference to the following Examples. Unless otherwise specified, reactions were carried out at atmospheric pressure in Examples and Comparative Examples as will be described hereinafter.

In Examples and Comparative Examples, the yield of and the selectivity for a produced para-substituted phenol derivative are respectively those obtained by the following formulae:

Yield of a para-substituted phenol derivative (%) = (1)

$$\frac{\text{mole number of produced para-substituted phenol derivative}}{\text{mole number of fed phenol}} \times 100$$

Selectivity for a para-substituted phenol derivative (%) = (2)

$$\frac{\text{mole number of produced para-substituted phenol derivative}}{\begin{pmatrix}\text{mole number} \\ \text{of produced} \\ \text{ortho-substituted} \\ \text{phenol derivative}\end{pmatrix} + \begin{pmatrix}\text{mole number} \\ \text{of produced} \\ \text{para-substituted} \\ \text{phenol derivative}\end{pmatrix}} \times 100$$

In Examples and Comparative Examples, there was produced no meta-substituted phenol derivative.

EXAMPLE 1

In 20 ml of an aqueous 20% sodium hydroxide solution were dissolved 1.5 g of phenol (first class grade reagent, manufactured and sold by Koso Chemical Co., Ltd., Japan) and 1.5 g of $\beta$-cyclodextrin (special grade reagent, manufactured and sold by Nakarai Chemical Ltd., Japan). To the resulting solution was added 3 ml of carbon tetrachloride (first class grade reagent, manufactured and sold by Tokyo Kasei Co., Ltd., Japan) and 0.1 g of copper powder (first class grade reagent, manufactured and sold by Yoneyama Yakuhin Kogyo Co., Ltd., Japan). The resulting mixture was allowed to react at 80° C. for 10 hours under reflux by the use of a reflux condenser while agitating by means of a magnetic stirrer. After completion of the reaction, the solution was acidified with hydrochloric acid, and subjected to extractions each with 50 ml of ethyl ether 3 times. The ethyl ether layer was washed with water, and then dried, thereby to obtain 2.1 g of a product. The infrared spectrum of the product thus obtained was in agreement with that of para-hydroxybenzoic acid (special grade reagent, Tokyo Kasei Co., Ltd., Japan). Further, the product was treated with chloroform and, as a result, it was found that the product did not contain any chloroform-soluble matter any more. Since both phenol if any remaining unreacted and salicylaldehyde if any formed as a side reaction product are readily soluble, in chloroform, the yield of the intended product was 95% and the selectivity was 100%.

COMPARATIVE EXAMPLE 1

Each reagent used herein was of the same grade as in Example 1. In 20 ml of an aqueous 20% sodium hydroxide solution was dissolved 1.5 g of phenol. To the resulting solution, 3 ml of carbon tetrachloride and 0.1 g of copper powder were added. The resulting mixture was allowed to react at 80° C. for 10 hours under reflux by the use of a reflux condenser while agitating by means of a magnetic stirrer. After completion of the reaction, the reaction mixture was acidified with hydrochloric acid, and subjected to extractions each with 50 ml of ethyl ether 3 times. The ethyl ether layer was washed with water, and then dried, thereby to obtain 2.1 g of a product. The product thus obtained was treated with chloroform to give 1.2 g of a chloroform-insoluble matter and 0.9 g of a chloroform-soluble matter. The infrared spectrum of the chloroform-insoluble matter was in agreement with that of para-hydroxybenzoic acid. On the other hand, the infrared spectrum of the chloroform-soluble matter was in agreement with that of salicylic acid (special grade reagent, manufactured and sold by Koso Chemical Co., Ltd., Japan). Namely, the yield of the intended product was 55% and the selectivity was 57%.

EXAMPLE 2

Substantially the same procedures as in Example 1 were repeated except that 1.5 g of o-cresol was used instead of 1.5 g of phenol and that the reaction was effected for 15 hours instead of 10 hours. The yield of and selectivity for the obtained 4-hydroxy-3-methylbenzoic acid were 57% and 97%, respectively.

EXAMPLE 3

Substantially the same procedures as in Example 1 were repeated except that β-cyclodextrin was used in an amount of 0.5 g instead of 1.5 g and that the reaction was effected for one hour instead of 10 hours. The yield of and selectivity for the obtained para-hydroxybenzoic acid were 12% and 99%, respectively.

EXAMPLE 4

Substantially the same procedures as in Example 1 were repeated except that β-cyclodextrin was used in an amount of 2.2 g instead of 1.5 g and that the reaction was effected for one hour instead of 10 hours. The yield of and selectivity for the obtained para-hydroxybenzoic acid were 37% and 100%, respectively.

EXAMPLE 5

In 50 ml of an aqueous 1% sodium hydroxide solution were dissolved 0.20 g of 2,4,6-trimethylphenol (special grade reagent, manufactured and sold by Tokyo Kasei Co., Ltd., Japan) and 7.5 g of α-cyclodextrin (special grade reagent, manufactured and sold by Nakarai Chemical Ltd., Japan). 0.9 g of allyl bromide (special grade reagent, manufactured and sold by Tokyo Kasei Co., Ltd., Japan) was gradually added to the resulting solution at room temperature (20° C.) so that the reaction was effected while maintaining the molar ratio of α-cyclodextrin to allyl bromide in the solution at 0.8 to 2. The reaction was continued for 24 hours. The control of the molar ratio of α-cyclodextrin to allyl bromide in the reaction system was effected as follows. Every two hours during the course of the reaction, part of the reaction mixture was taken and subjected to the determination of allyl bromide contained therein by means of 701-type Gas Chromatograph manufactured by Ohkura Rikagaku Kenkyusho Co., Ltd., Japan (packing material, Porapak Q manufactured and sold by Gasukuro Kogyo Inc., Japan; column length 2 m; column temperature, 30° C.; carrier gas, helium), and the rate of the addition of allyl bromide to the reaction system was adjusted so that the molar ratio of α-cyclodextrin to allyl bromide was maintained at 0.8 to 2.

After completion of the reaction, the reaction mixture was subjected to extractions each with 50 ml of ether 5 times. The ether layer was dried to obtain 0.18 g of a product. The $^1$H-NMR measurement showed that the product was a mixture of 53% of 2,4,6-trimethyl-4-allyl-2,5-cyclohexadienone, 26% of 2,4,6-trimethyl-6-allyl-2,4-cyclohexadienone and 21% of 2,4,6-trimethylphenyl allyl ether. Namely, the yield of the intended product and the selectivity were 37% and 53%, respectively.

COMPARATIVE EXAMPLE 2

Substantially the same procedures as in Example 5 were repeated except that the use of 7.5 g of α-cyclodextrin was omitted. After completion of the reaction, the reaction mixture was subjected to extractions each with 50 ml of ether 5 times. The ether layer was dried to obtain 0.19 g of a product. The $^1$H-NMR measurement showed that the product was a mixture of 25% of 2,4,6-trimethyl-4-allyl-2,5-cyclohexadienone, 50% of 2,4,6-trimethyl-6-allyl-2,4-cyclohexadienone and 25% of 2,4,6-trimethylphenyl allyl ether. Namely, the yield of the intended product and the selectivity were 18% and 25%, respectively.

EXAMPLE 6

Substantially the same procedures as in Example 5 were repeated except that 7.5 g of β-cyclodextrin (special grade reagent, manufactured and sold by Nakarai Chemical Ltd., Japan) was used instead of 7.5 g of α-cyclodextrin. There was obtained 0.20 g of a product. The $^1$H-NMR measurement showed that the product was a mixture of 41% of 2,4,6-trimethyl-4-allyl-2,5-cyclohexadienone, 32% of 2,4,6-trimethyl-6-allyl-2,4-cyclo-hexadienone and 27% of 2,4,6-trimethylphenyl allyl ether. Namely, the yield of the intended product and selectivity were 32% and 41%, respectively.

EXAMPLE 7

In accordance with the method as described in J. Amer. Chem. Soc., 102,762 (1980), all of the primary hydroxyl groups of α-cyclodextrin were substituted by N-methylformamido groups. In 50 ml of an aqueous 1% sodium hydroxide solution were dissolved 8 g of the above-obtained modified cyclodextrin and 0.20 g of 2,4,6-trimethylphenol. The reaction of 2,4,6-trimethylphenol with allyl bromide was effected in substantially the same manner as in Example 5.

After completion of the reaction, the reaction mixture was subjected to extractions each with 50 ml of ethyl ether 5 times. The ethyl ether layer was dried to obtain 0.22 g of a product. The $^1$H-NMR measurement showed that the product was entirely 6-trimethyl-4-allyl-2,5-cyclohexadienone. Namely, the yield of the product and selectivity were 85% and 100%, respectively.

What is claimed is:

1. A process for producing a para-substituted phenol derivative which comprises reacting a phenol compound represented by the formula (I)

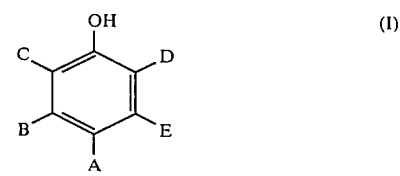

wherein A, B, C, D and E each independently stand for hydrogen, a hydroxyl group, a substituted or unsubstituted alkyl group, a substituted or unsubstituted allyl group, a substituted or unsubstituted alkoxyl group or a substituted or unsubstituted aryl group, provided that A does not stand for a hydroxyl group and that when two or more of A, B, C, D, and E each independently stand for a substituted or unsubstituted alkyl group or a substituted or unsubstituted alkoxyl group, they have their respective free terminal ends or at least one of them is bonded to another group selected from said alkyl and alkoxyl groups to form a ring,
with an organic halide selected from the group consisting of a carbon tetrahalide and a substituted or unsubstituted allyl halide in the presence of an alkali metal hydroxide, using as a catalyst a modified or unmodified cyclodextrin, thereby to introduce a substituent group derived from said organic halide to the para-position of the phenol compound.

2. A process according to claim 1, wherein said substituted or unsubstituted alkyl group, said substituted or unsubstituted allyl group, said substituted or unsubstituted alkoxyl group and said substituted or unsubstituted aryl group each have carbon atoms of not more than 6 with respect to B, C, D and E and each have carbon atoms of not more than 12 with respect to A.

3. A process according to claim 1, wherein said alkali metal hydroxide is sodium hydroxide or potassium hydroxide.

4. A process according to claim 1, wherein said alkali metal hydroxide is employed in an amount of 1 to 15 times the stoichiometrical amount of said alkali metal hydroxide relative to said phenol compound.

5. A process according to claim 1, wherein said organic halide is employed in an amount of 1 to 20 in terms of molar ratio with respect to said phenol compound.

6. A process according to claim 1, wherein said modified or unmodified cyclodextrin is employed in an amount of 0.001 to 20 in terms of molar ratio with respect to said organic halide.

7. A process according to claim 1, wherein the reaction is effected at 0° to 120° C.

8. A process according to claim 1, said organic halide is a substituted or unsubstituted allyl halide and said cyclodextrin is a modified one.

9. A process according to claim 1, wherein the reaction is effected in an aqueous medium.

10. A process according to claim 1, wherein A in the formula (I) is hydrogen and said para-substituted phenol derivative is represented by the formula (II)

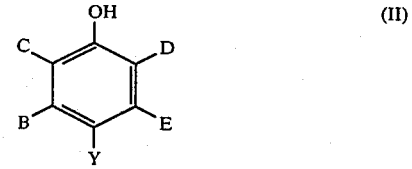

(II)

wherein B, C, D and E are as defined above and Y stands for a substituted or unsubstituted allyl group or a carboxyl group,
or A in the formula(I) is a substituted or unsubstituted alkyl group, a substituted or unsubstituted allyl group, a substituted or unsubstituted alkoxyl group or a substituted or unsubstituted aryl group and said para-substituted phenol derivative is represented by the formula(III)

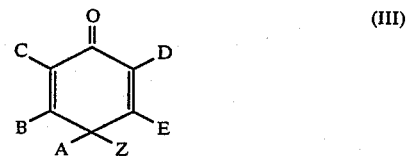

(III)

wherein A, B, C, D and E are as defined above, provided that A does not stand for hydrogen, and Z stands for a substituted or unsubstituted allyl group.

* * * * *